US 11,179,411 B2

(12) United States Patent
Inoue et al.

(10) Patent No.: US 11,179,411 B2
(45) Date of Patent: Nov. 23, 2021

(54) COMPOSITION FOR PREVENTION OR TREATMENT OF SPINOCEREBELLAR ATAXIA TYPE 36

(71) Applicant: KYOTO UNIVERSITY, Kyoto (JP)

(72) Inventors: Haruhisa Inoue, Kyoto (JP); Keiko Imamura, Kyoto (JP); Kosuke Matsuzono, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/614,644

(22) PCT Filed: May 17, 2018

(86) PCT No.: PCT/JP2018/019082
§ 371 (c)(1),
(2) Date: Nov. 18, 2019

(87) PCT Pub. No.: WO2018/212271
PCT Pub. Date: Nov. 22, 2018

(65) Prior Publication Data
US 2020/0222443 A1    Jul. 16, 2020

(30) Foreign Application Priority Data
May 18, 2017    (JP) .............................. JP2017-099374

(51) Int. Cl.
*C12N 15/113*    (2010.01)
*A61K 48/00*    (2006.01)
*A61K 31/7088*    (2006.01)

(52) U.S. Cl.
CPC .......... *A61K 31/7088* (2013.01); *A61K 48/00* (2013.01); *C12N 15/113* (2013.01)

(58) Field of Classification Search
CPC .... A61K 31/7088; C12N 15/113; A61P 25/00
See application file for complete search history.

(56) References Cited

U.S. PATENT DOCUMENTS

| | | | | |
|---|---|---|---|---|
| 2005/0164968 A1* | 7/2005 | McSwiggen ... | C12Y 301/03048 | 514/44 A |
| 2011/0184050 A1* | 7/2011 | De Kimpe | .............. | A61P 21/00 514/44 R |
| 2014/0024698 A1* | 1/2014 | Kole | .......... | A61P 9/10 514/44 A |
| 2014/0303238 A1 | 10/2014 | Linsley et al. | | |
| 2015/0247141 A1* | 9/2015 | Uhlmann | .............. | C12N 15/111 514/44 A |
| 2015/0259679 A1* | 9/2015 | Bennett | .................. | A61P 25/00 514/44 A |

FOREIGN PATENT DOCUMENTS

| JP | 2015-506669 A | 3/2015 |
|---|---|---|
| WO | 2017/216771 A2 | 12/2017 |
| WO | 2017/216771 A3 | 12/2017 |

OTHER PUBLICATIONS

Spinocerebellar ataxia, Genetic and Rare Diseases Information Center (GARD), 2017, 10 pages, retrieved from https://rarediseases.info.nih.gov/diseases/10748/spinocerebellar-ataxia (Year: 2017).*
Gendron et al (Cold Spring Harb Perspect Med doi: 10.1101/cshperspect.a024224, 2017) (Year: 2017).*
International Search Report (ISR) issued in PCT/JP2018/019082 dated Aug. 7, 2018.
Kobayashi, et al., "Expansion of Intronic GGCCTG Hexanucleotide Repeat in NOP56 Causes SCA36, a Type of Spinocerebellar Ataxia Accompanied by Motor Neuron Involvement", The American Journal of Human Genetics, Jul. 15, 2011, vol. 89, pp. 121-130; Cited in Specification.
Ikeda, et al., "Clinical features of SCA36: a novel spinocerebellar ataxia with motor neuron involvement (Asidan)", Neurology, Jul. 24, 2012, vol. 79, pp. 333-341; English abstract only; Cited in Specification.
Liu, et al., "Characteristic RNA foci of the abnormal hexanucleotide GGCCUG repeat expansion in spinocerebellar ataxia type 36 (Asidan)", European Journal of Neurology, 2014, vol. 21, pp. 1377-1386; Cited in Specification and ISR.
Donnelly, et al., "RNA toxicity from the ALS/FTD C9ORF72 expansion is mitigated by antisense intervention", Neuron, 2013, vol. 80, pp. 415-428; Cited in Specification and ISR.
Jiang, et al., "Gain of toxicity from ALS/FTD-linked repeat expansions in C9ORF72 is alleviated by antisense oligonucleotides targeting GGGGCC-Containing RNAs", Neuron, 2016, vol. 90, pp. 535-550; Cited in Specification.
Hayano, et al., "Proteomic Analysis of Human Nop56p-associated Pre-ribosomal Ribonucleoprotein Complexes" Journal of Biological Chemistry, 2003, vol. 278, No. 36, p. 34309-34319; Cited in Specification.
Gautier, et al., "Nucleolar KKE/D Repeat Proteins Nop56p and Nop58p Interact with Nop1p and Are Required for Ribosome Biogenesis", Molecular and Cellular Biology, Dec. 1997, vol. 17, pp. 7088-7098; Cited in Specification.
Abe et al., "Molecular pathology of Asidan/SCA36", Annual Review Neurology, 2014, pp. 18-26 and its English abstract; Cited in ISR.
Leger et al., "Systemic Delivery of a Peptide-Linked Morpholino Oligonucleotide Neutralizes Mutant RNA Toxicity in a Mouse Model of Myotonic Dystrophy" Nucleic Acid Therapeutics, Nov. 2, 2013, vol. 23, pp. 109-117; Cited in ISR.
Wheeler et al., "Reversal of RNA Dominance by Displacement of Protein Sequestered on Triplet Repeat RNA", Science, Jul. 17, 2009, vol. 325, pp. 336-339; Cited in ISR.

(Continued)

*Primary Examiner* — Richard A Schnizer
(74) *Attorney, Agent, or Firm* — Rankin, Hill & Clark LLP

(57) ABSTRACT

An object of the present invention is to provide ASO that can effectively suppress a formation of RNA foci spontaneously occurring in neurons having SCA36 mutation, without inducing the cleavage of NOP56 pre-mRNA. The present invention provides an oligonucleotide comprising a nucleotide sequence in which one or more nucleotide sequences represented by SEQ ID NO: 2 are consecutively connected and is complementary to pre-mRNA of NOP56 gene, wherein a structure formed by the hybridization of the oligonucleotide to the pre-mRNA is resistant to RNaseH.

8 Claims, 4 Drawing Sheets
Specification includes a Sequence Listing.

(56) References Cited

OTHER PUBLICATIONS

Loureiro et al., "Unstable repeat expansions in neurodegenercitive diseases: nucleocytoplasmic transport emerges an the scene", Neurobiology of Aging, ELSEVIER, 2016, vol. 39, pp. 174-183, Cited in ISR.
Sicot et al., "RNA toxicity in human disease and animal models: From the uncovering of a new mechanism to the development of promising therapies", Biochimica et Biophysica Acta, ELSEVIER, 2013, vol. 1832, pp. 1390-1409; Cited in ISR.
Zhang et al., "RNA toxicity and foci formation in misrosatellite expansion diseases", ScienceDirect, Current Opinion in Genetics & Development, ELSEVIER, 2017, vol. 44, pp. 17-29; Cited in ISR.
Kole et al., "RNA therapeutics: beyond RNA interference and antisense oligonucleotides", Nature Reviews Drug Discovery, Feb. 2012, vol. 11, pp. 125-140; Cited in ISR.
Evers et al., "Antisense oligonucleotides in therapy for neurodegenerative disorders", Advanced Drug Delivery Reviews, ELSEVIER, 2015, vol. 87, pp. 90-103; Cited in ISR.
Matsuzono et al., "Modeling spinocerebellar ataxia type 36 using patient induced pluripotent stem cells", Clinical Neurology, 2016, vol. 56, p. S283; Cited in ISR.
Matsuzono K et al., "Antisense Oligonucleotides Reduce RNA Foci in Spinocerebellar Ataxia 36 Patient iPSCs" Molacular Therapy: Nucleic Acids, Sep. 2017, vol. 8, pp. 211-219; Cited in ISR.
Zarouchlioti C et al., "Antisense Therapy for a Common Comeal Dystrophy Ameliorates TCF4 Repeat Expansion-Mediated Toxicity", The American Journal of Human Genetics, Apr. 5, 2018, vol. 102, pp. 528-539; Cited in ISR.
Extended European Search Report (EESR) dated Jan. 29, 2021 issued in the corresponding European Patent Application No. 18802436.8.

\* cited by examiner

[Figure 1]
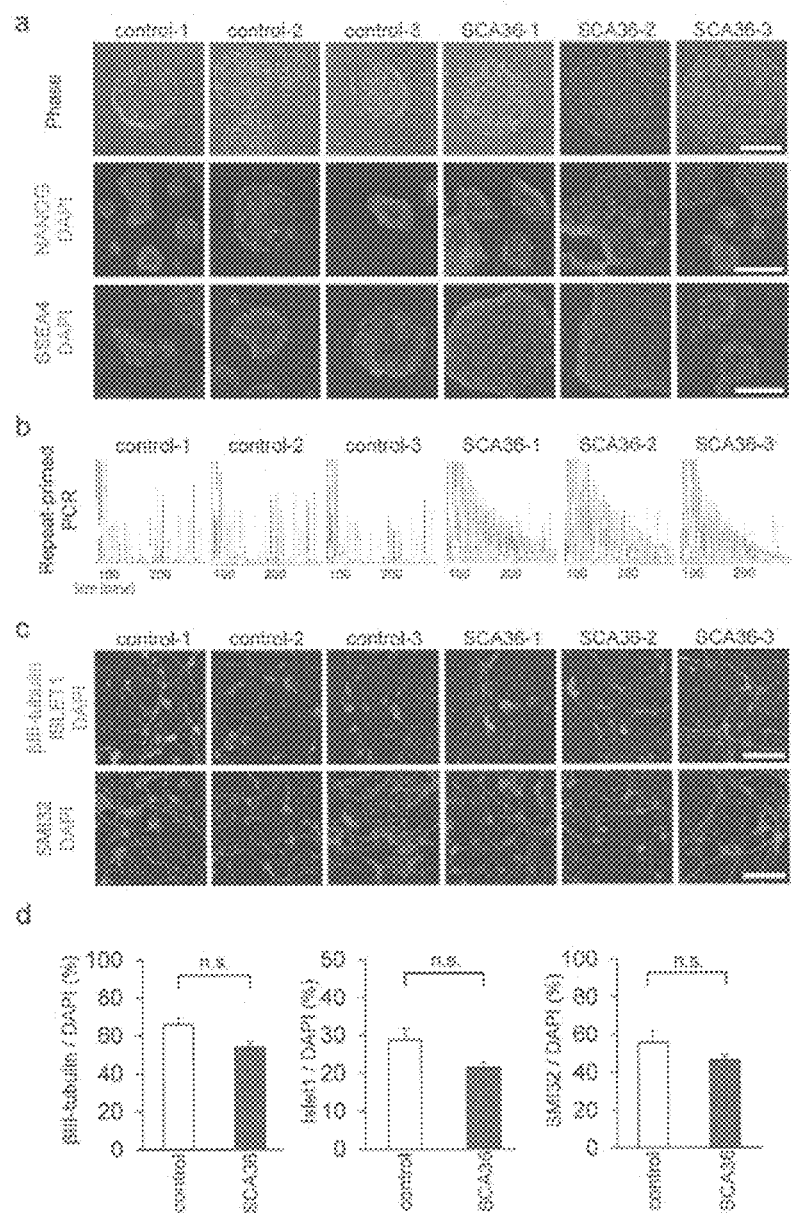

[Figure 2]
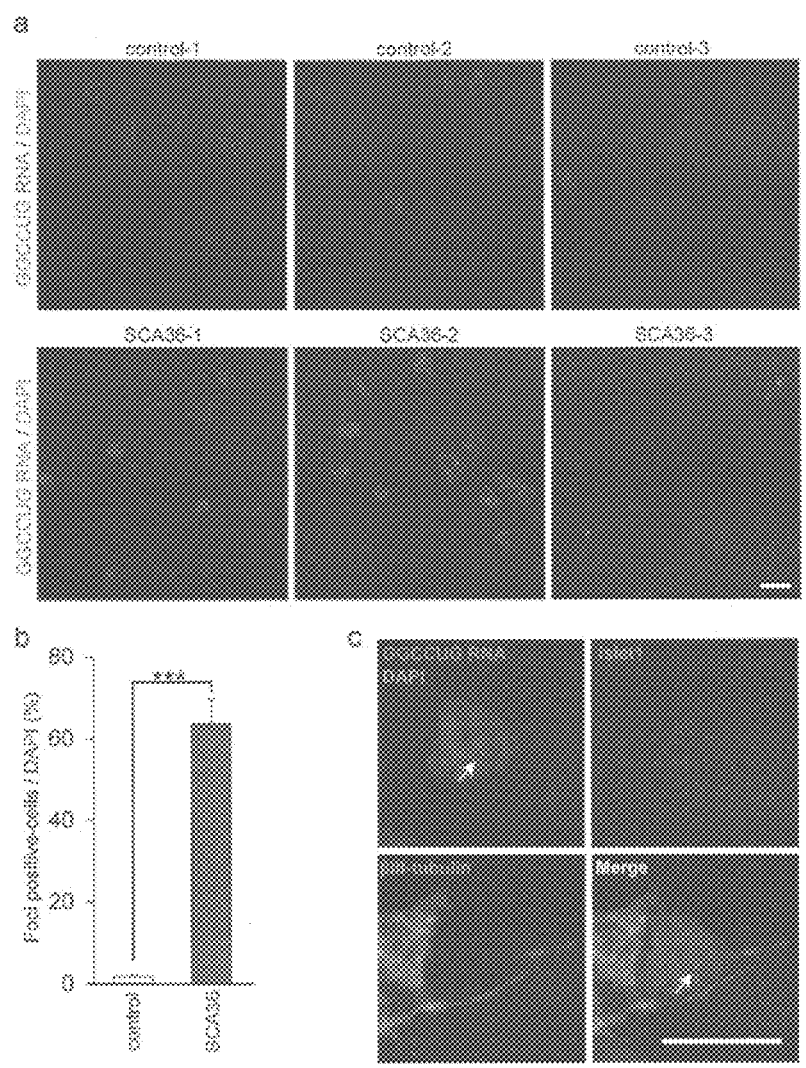

[Figure 3]
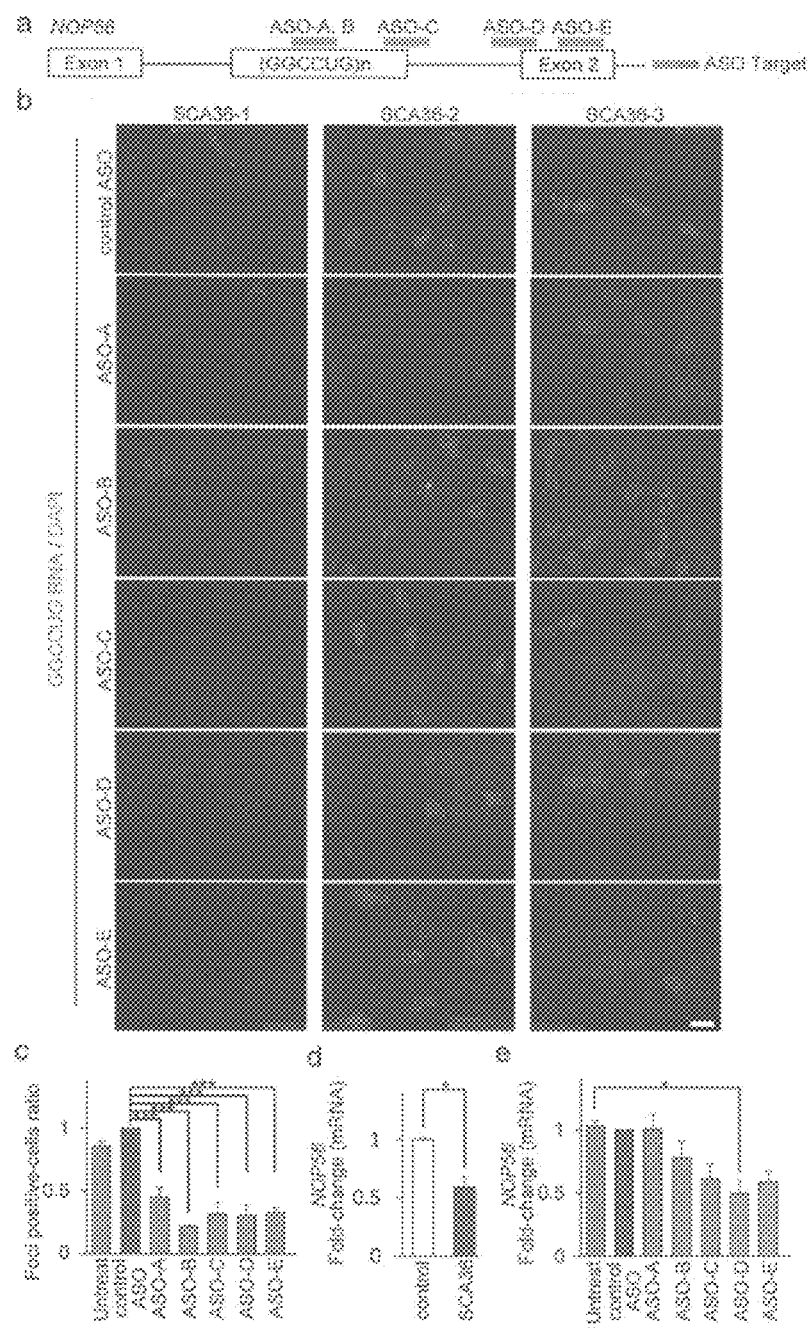

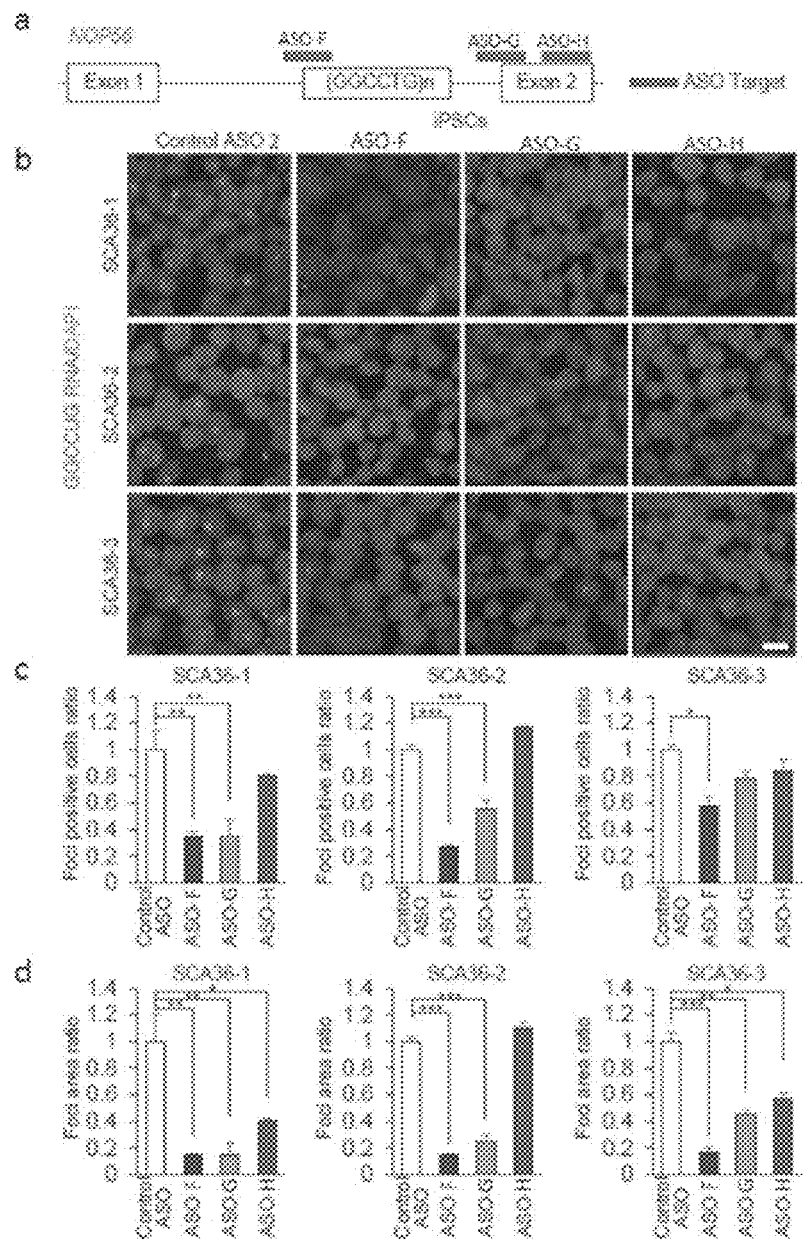
[Figure 4]

COMPOSITION FOR PREVENTION OR TREATMENT OF SPINOCEREBELLAR ATAXIA TYPE 36

RELATED APPLICATIONS

The present application claims the priority of Japanese Patent Application No. 2017-099374 filed on May 18, 2017, which is incorporated herein.

FIELD OF THE INVENTION

The present invention relates to a composition for prevention or treatment of spinocerebellar ataxia type 36. More specifically, the present invention relates to the composition comprising an antisense nucleic acid targeting NOP56 gene.

BACKGROUND OF THE INVENTION

Spinocerebellar ataxia (SCA) is an intractable neurological disease involving motor incoordination as a main symptom and neuronal degeneration or loss from the cerebellum and the brain stem through the spinal cord. In Japan, approximately 30,000 patients have been recognized, and approximately 30% of these cases are inherited.

Inherited spinocerebellar ataxia is classified depending on a causative gene thereof, and type 1 to type 36 have been reported so far. Among them, type 36 (spinocerebellar ataxia type 36: SCA36) is a disease that has been found in Japan, and has been shown to be caused by the abnormal expansion of GGCCTG (SEQ ID NO: 1) repeats residing in intron 1 of NOP56 gene (Non Patent Literatures 1 and 2). From the analysis of autopsied tissues from SCA36 patients, it has further been reported that a structure where other RNAs or proteins aggregate (called RNA foci) with the repeat region in NOP56 pre-mRNA as a core is specifically formed in neurons of an affected area. This formation of RNA foci is considered to be deeply involved in the onset of the disease (Non Patent Literature 3). This is because: for neurodegenerative diseases caused by the abnormal expansion of a repeat sequence in a particular gene, RNA foci are often formed in neurons of a lesion site (e.g., Non Patent Literature 4); and it is known that the suppression of the formation of the RNA foci ameliorates symptoms in the model animals (e.g., Non Patent Literature 5).

Meanwhile, techniques related to nucleic acid drugs have made remarkable progress in recent years, and these drugs have raised big expectations as next-generation drugs following antibody drugs.

The nucleic acid drugs generally refer to "drugs that contain an oligonucleic acid with linearly bonded nucleic acids or modified nucleic acids as an active pharmaceutical ingredient, are capable of acting directly on organisms without the mediation of proteins, and are produced by chemical synthesis". Examples of the nucleic acid drugs that function in the inside of cells include antisense oligonucleotides (hereinafter, also abbreviated to ASOs) and siRNA. A plurality of ASOs have already been approved as drugs.

ASOs are broadly classified into gapmer type and block type according to difference in the mechanism of action.

The gapmer ASO is ASO capable of inducing the cleavage of target RNA by RNaseH. RNaseH is an endoribonuclease that is universally present in cells and recognizes a DNA/RNA duplex structure and thereby cleaves the RNA. Hence, the gapmer ASO generally has a structure having a central region consisting of deoxyribonucleotides so as to be able to stably form the DNA/RNA duplex structure by hybridizing to target RNA, and nuclease-resistant modified nucleotides flanking the region.

By contrast, the block ASO is ASO capable of inhibiting the function of target RNA through binding, without inducing the cleavage of the target RNA by RNaseH. Typical examples thereof include splicing-controlling type which binds to the splicing control site of target RNA and thereby changes the splicing pattern of the RNA, and miRNA-inhibiting type which binds to miRNA and thereby blocks the ability of the miRNA to hybridize (to another RNA).

Among them, the gapmer ASO has achieved the best performance as a nucleic acid drug. This is because the gapmer ASO cleaves target RNA itself and is therefore capable of irreversibly inhibiting harmful effects resulting from the presence of the target RNA. However, the cleavage of the target RNA also inhibits protein expression from the RNA. Therefore, the application of the gapmer ASO to cases where the arrest of the protein expression or decreased expression levels thereof become problematic is limited in the circumstances.

NOP56 protein encoded by the NOP56 gene is a constituent of box C/D small nucleolar ribonucleoprotein complexes responsible for the processing of pre-rRNA necessary for the assembly of 60S ribosomal subunits (Non Patent Literature 6). Furthermore, it has been reported as to temperature-sensitive mutants of budding yeast NOP56 gene that the assembly of 60S ribosomal subunits is inhibited at high temperatures due to the disrupted processing of pre-rRNA so that the mutants become inviable (Non Patent Literature 7).

Under these circumstances, it is probably desirable for inhibiting the formation of RNA foci with NOP56 pre-mRNA having SCA36 mutation as a core to use ASO that does not induce the cleavage of the pre-mRNA (i.e., block ASO). However, the mechanism of action of the block ASO is basically steric hindrance resulting from the binding of an ASO molecule to target RNA. In the case of target RNA having a small chain length, the purpose may be attained by the binding of ASO throughout the whole length thereof (e.g., miRNA-inhibiting ASO). In the case of target RNA having a large chain length, it is necessary for eliminating unknown influence ascribable to the administration of excess ASO to select a site to be bound (target sequence). In this respect, it may be easy to list candidates of the target sequence for the purpose of changing the splicing pattern of target RNA (e.g., splicing-controlling ASO), whereas it is very difficult to discuss the target sequence for the purpose of inhibiting the formation of RNA foci caused by the abnormal expansion of the repeat sequence. This is because there is no effective suggestion about a portion to be noted for a sequence having hundreds of consecutive repeats of the same sequence.

Since the RNA foci are aggregates of other RNAs or proteins bound to the repeat region, the administration of ASO capable of binding to the repeat region might further promote the aggregation.

Thus, there has been a demand for the development of ASO capable of effectively suppressing the formation of RNA foci occurring in the inside of neurons having SCA36 mutation, without inducing the cleavage of NOP56 pre-mRNA, though a specific path thereto has been unknown.

CITATION LIST

Non Patent Literature

[Non Patent Literature 1] Kobayashi, H, Abe, K, Matsuura, T, Ikeda, Y, Hitomi, T, Akechi, Y, et al. (2011). Expansion of intronic GGCCTG hexanucleotide Repeat in NOP56 Causes SCA36, a type of Spinocerebellar ataxia accompanied by Motor Neuron Involvement. Am J Hum Genet 89: 121-130.
[Non Patent Literature 2] Ikeda, Y, Ohta, Y, Kobayashi, H, Okamoto, M, Takamatsu, K, Ota, T, et al. (2012). Clinical features of SCA36 A novel spinocerebellar ataxia with motor neuron involvement (Asidan). Neurology 79: 333-341.
[Non Patent Literature 3] Liu, W, Ikeda, Y, Hishikawa, N, Yamashita, T, Deguchi, K, and Abe, K (2014). Characteristic RNA foci of the abnormal hexanucleotide GGCCUG repeat expansion in spinocerebellar ataxia type 36 (Asidan). Eur J Neurol 21: 1377-1386.
[Non Patent Literature 4] Donnelly, C J, Zhang, P W, Pham, J T, Heusler, A R, Mistry, N A, Vidensky, S, et al. (2013), RNA toxicity from the ALS/FTD C9ORF72 expansion is mitigated by antisense intervention. Neuron 80: 415-428.
[Non Patent Literature 5] Jiang, J, et al. (2016). Gain of toxicity from ALS/FTD-linked repeat expansions in C9ORF72 is alleviated by antisense oligonucleotides targeting GGGGCC-Containing RNAs. Neuron 90: 535-550.
[Non Patent Literature 6] Hayano, T., Yanagida, M., Yamauchi, Y., Shinkawa, T., Isobe, T., and Takahashi, N (2003). Proteomic analysis of human Nop56p-associated pre-ribosomal ribonucleoprotein complexes: possible link between Nop56p and the nucleolar protein treacle responsible for Treacher Collins syndrome. J. Biol. Chem. 278: 34309-34319.
[Non Patent Literature 7] Gautier, T., Berges, T., Tollervey, and D., Hurt, E (1997). Nucleolar KKE/D repeat proteins Nop56p and Nop58p interact with Nop1p and are require for ribosome biogenesis. Mol. Cell. Biol. 17: 7088-7098.

DISCLOSURE OF THE INVENTION

Problem to be Solved by the Invention

The present invention has been made in light of the problems of the conventional techniques. An object of the present invention is to provide ASO that can effectively suppress a formation of RNA foci spontaneously occurring in neurons having SCA36 mutation, without inducing the cleavage of NOP56 pre-mRNA.

Means to Solve the Problem

In order to attain the object, the present inventor has established iPSCs from SCA36 patients, and induced the differentiation of the iPS to neurons to obtain human neurons that spontaneously form RNA foci (SCA36-iPSNs). By using the SCA36-iPSNs as an analysis system, the present inventor has found that ASO that has a nucleotide sequence in which one or more nucleotide sequences complementary to a GGCCUG sequence (SEQ ID NO: 2) are consecutively connected, and does not induce the cleavage of the pre-mRNA by RNaseH, can effectively suppress a formation of RNA foci in neurons having SCA36 mutation. The present invention has been completed on the basis of the findings.

The present invention encompasses aspects given below. SEQ ID NO: 2 refers to a nucleotide sequence (CAGGCC) complementary to the repeat unit (GGCCUG, SEQ ID NO: 3) of a repeat region existing residing in intron 1 of NOP56 pre-mRNA.

[1]
An oligonucleotide comprising a nucleotide sequence in which one or more sequences represented by SEQ ID NO: 2 are consecutively connected, wherein the oligonucleotide is complementary to pre-mRNA of NOP56 gene; and
a structure formed by the hybridization of the oligonucleotide to the pre-mRNA is resistant to RNaseH.

[2]
The oligonucleotide according to [1], wherein the oligonucleotide does not comprise four or more consecutive deoxynucleosides.

[3]
The oligonucleotide according to [1] or [2], wherein the oligonucleotide comprises 20% or more nucleosides with a modified sugar moiety in all nucleosides.

[4]
The oligonucleotide according to [3], wherein the nucleosides with a modified sugar moiety are one or more types of nucleosides with a modified sugar moiety selected from 2'-modified nucleosides, cross-linked nucleosides, and substituted nucleosides.

[5]
The oligonucleotide according to [4], wherein the 2'-modified nucleosides are one or more types of 2'-modified nucleosides selected from 2'-fluoronucleoside, 2'—O-methylnucleoside, and 2'—O-methoxyethylnucleoside.

[6]
The oligonucleotide according to [4], wherein the cross-linked nucleosides are one or more types of cross-linked nucleosides selected from BNA, ENA, and LNA.

[7]
The oligonucleotide according to [4], wherein the substituted nucleosides are morpholino.

[8]
The oligonucleotide according to any of [1] to [6], wherein the oligonucleotide has at least one or more modified internucleoside bonds.

[9]
The oligonucleotide according [8], wherein the modified internucleoside bonds are phosphorothioate internucleoside bonds.

[10]
The oligonucleotide according to any of [1] to [9], wherein the oligonucleotide consists of 18 to 30 nucleotides.

[11]
The oligonucleotide according to any of [1] to [10], wherein the oligonucleotide has a nucleotide sequence represented by SEQ ID NO: 4 or 10.

[12]
A composition for prevention or treatment of spinocerebellar ataxia type 36, comprising an oligonucleotide according to any of [1] to [11] as an active ingredient.

Effect of the Invention

The present invention provides an antisense oligonucleotide that can effectively suppress RNA foci formation in human neurons having SCA36 mutation, without inducing the cleavage of NOP56 pre-mRNA. The present invention also provides a composition for prevention or treatment of SCA36 under the mechanism of inhibiting the formation of RNA foci.

BRIEF DESCRIPTION OF THE DRAWINGS

In the present specification, cells obtained by inducing the differentiation of iPSCs into neurons are also referred to as iPSNs. In the present specification, mRNA (having introns) before removal of introns by splicing is referred to as pre-mRNA, and mRNA from which the introns have been removed is referred to as mRNA.

In drawings given below, Control-1 to Control-3 depict results about iPSCs or iPSNs derived from three healthy subjects, and SCA36-1 to SCA36-3 depict results about iPSCs or iPSNs derived from three SAC36 patients. Error bars in graphs represent mean±standard deviation (n=3). Asterisks (*) in the drawings represent that significance with p value<0.05 was confirmed as a result of a significance test; double asterisks () represent that significance with p value<0.01 was confirmed; and double asterisks () represent that significance with p value<0.001 was confirmed.

FIG. 1a shows results of analyzing the expression of undifferentiation markers NANOG (green) and SSEA4 (red) by use of an immunostaining method for iPSCs established from somatic cells derived from healthy subjects and SAC36 patients. The bars in the drawing represent 500 μm. FIG. 1b shows results of analyzing the number of GGCCTG repeats in intron 1 of NOP56 gene by use of repeat-primed PCR for iPSCs established from somatic cells derived from healthy subjects and SAC36 patients. FIG. 1c shows results of analyzing the expression of a neuron marker protein (β-III tubulin, green) and motor neuron marker proteins (Islet1 and SMI32, both red) by use of an immunostaining method for iPSNs established from iPSCs derived from healthy subjects and SAC36 patients. The bars in the drawing represent 50 μm. FIG. 1d shows results of comparing the ratio of the number of β-III tubulin-positive cells (left panel), the number of Islet1-positive cells (central panel), or the number of SMI32-positive cells (right panel) to the total number of cells (i.e., the number of DAPI-positive cells) between Control-iPSNs and SAC36-iPSNs in FIG. 1c.

FIG. 2a shows results of analyzing the presence or absence of RNA foci with a repeat region having repeats of GGCCUG (SEQ ID NO: 3) in NOP56 pre-mRNA as a core by use of FISH for Control-iPSNs and SAC36-iPSNs. The bar in the drawing represents 10 μm. FIG. 2b is a graph plotting the ratio of the number of cells having the RNA foci (the number of cells of 60 μm or larger in diameter having a Cy3 signal in the nucleus) to the total number of cells (the number of DAPI-positive cells) in the analysis of FIG. 2a. FIG. 2c shows immunostaining results showing that RNA foci were formed in the nuclei of β-III tubulin-positive cells (neurons) and Islet1-positive cells (motor neurons)

FIG. 3a is a schematic diagram showing a portion (region from exon 1 to exon 2) of NOP56 pre-mRNA and target sites of five types of ASOs (ASO-A to ASO-E). FIG. 3b shows immunostaining results of analyzing the formation of RNA foci 48 hours after introduction of any one ASO selected from ASO-A to ASO-E and Control ASO1 to SAC36-iPSNs. FIG. 3c is a graph in which the number of cells having RNA foci was measured in FIG. 3b, and the number of the cells in iPSNs harboring any of ASO-A to ASO-E was indicated by a relative value to the number of the cells in iPSNs harboring Control ASO1. FIG. 3d is a graph in which the expression level of NOP56 mRNA was comparatively analyzed between iPSNs derived from healthy persons and SCA36 patients without the introduction of ASO. FIG. 3e shows results of analyzing the expression level of NOP56 mRNA in the iPSNs of FIG. 3b.

FIG. 4a is a schematic diagram showing a portion (region from exon 1 to exon 2) of NOP56 pre-mRNA and target sites of three types of ASOs (ASO-F to ASO-H). FIG. 4b shows immunostaining results of analyzing the formation of RNA foci 48 hours after introduction of any one ASO selected from ASO-F to ASO-H and Control ASO2 to SAC36-iPSNs. FIG. 4c is a graph in which the number of cells having RNA foci was measured in FIG. 4b and indicated by a relative value to the number of the cells in iPSNs harboring Control ASO2. FIG. 4d is a graph in which the total area of RNA foci was measured in FIG. 4b and indicated by a relative value to the total area in iPSNs harboring Control ASO2.

BEST MODE FOR CARRYING OUT THE INVENTION

Hereinafter, preferred embodiments of the present invention will be described in detail. The NOP56 gene according to the present invention is human NOP56 gene.

Spinocerebellar Ataxia Type 36 and NOP56 Gene

Spinocerebellar ataxia type 36 (also abbreviated to SCA36) is an inherited autosomal dominant neurodegenerative disease that has received attention as a crossover disease between spinocerebellar ataxia and motor neuron disease because motor neuron signs similar to those of amyotrophic lateral sclerosis (ALS), such as lingual atrophy or group atrophy of muscle fibers are found in addition to cerebellar ataxia typical to spinocerebellar ataxia. This disease has been found by a Japanese researcher and shown to be caused by the abnormal expansion of GGCCTG repeats residing in intron 1 of NOP56 gene encoding nucleolar protein 56 (abbreviated to NOP56) protein (NP_006383). The number of the repeats falls within the range of approximately 3 to 14 for healthy persons, but is expanded even to approximately 650 to 2,500 for SCA36 patients. Thus, the disease is also characterized by larger difference in the number of repeats between healthy subjects and patients than that of other repeat diseases (e.g., ALS/FTD caused by the abnormal expansion of GGGGCC repeats in C9ORF72 gene) (Non Patent Literatures 1 to 3).

It is known as to some repeat diseases that large aggregates (RNA foci) are formed by the aggregation of other RNAs or proteins with, as a core, an abnormally expanded repeat region in pre-mRNA transcribed from a causative gene in affected neurons of the diseases (Non Patent Literature 4). It has further been reported that when ASO that binds to the pre-mRNA and thereby induces its degradation by RNaseH is administered to model insects and model mice having the mutated gene, toxicity derived from the mutated gene is mitigated (Zhang, K, et al., (2015). The C9orf72 repeat expansion disrupts nucleocytoplasmic transport. Nature 525: 56-61, and Non Patent Literature 5).

Oligonucleotide Effectively Suppressing SCA36 RNA Foci

The oligonucleotide according to the present invention is capable of effectively suppressing the formation of RNA foci spontaneously occurring in human neurons having SCA36 mutation (also referred to as SCA36 RNA foci), without inducing the cleavage of NOP56 pre-mRNA. In this context, the SCA36 mutation refers to a mutation to abnormally increase the number of repeated GGCCTG (SEQ ID NO: 1) sequences (the number of repeats) residing in intron 1 of NOP56 gene. In the present application, the number of repeats of 600 or more is regarded as being abnormal. Accordingly, the SCA36 RNA foci refer to RNA foci formed with an abnormally expanded GGCCTG repeat region in intron 1 of human NOP56 pre-mRNA as a core. In the present application, the SCA36 RNA foci are also simply referred to as RNA foci.

The oligonucleotide according to the present invention is an oligonucleotide that has a nucleotide sequence in which one or more nucleotide sequences represented by SEQ ID NO: 2 are consecutively connected. Also, the oligonucleotide according to the present invention is complementary to pre-mRNA of NOP56 gene (i.e., ASO). The oligonucleotide binds to at least a portion of a repeat region of NOP56 pre-mRNA and then does not induce the cleavage of NOP56 pre-mRNA by RNaseH. Hence, it is required that the oligonucleotide according to the present invention should not comprise four or more consecutive deoxynucleosides. This is because RNaseH recognizes a RNA-DNA hetero duplex structure having a length of 4 base pairs or longer as a substrate. Accordingly, the oligonucleotide according to the present invention may comprise deoxyribonucleosides, ribonucleosides, and a mixture thereof as long as the oligonucleotide satisfies this condition. In the present specification, the "binding" of ASO to target RNA refers to "hybridization" to the target RNA.

The oligonucleotide according to the present invention is preferably modified without inhibiting its binding to NOP56 pre-mRNA, from the viewpoint of improvement in stability. Examples of such a modification include sugar moiety modification and base moiety modification.

Examples of the nucleosides with a modified sugar moiety that can be suitably used in the present invention include 2'-modified nucleosides, cross-linked nucleosides, and substituted nucleosides.

Examples of the 2'-modified nucleosides include nucleosides in which the OH group at position 2' of sugar is substituted with a group selected from H, OR, R, SH, SR, $NH_2$, NHR, $NR_2$, CN, and halogen. The R is C1-C6, preferably a C1-C6 alkyl group, alkoxy group, alkenyl group, or alkynyl group, particularly preferably a methyl group, an ethyl group, a methoxyethyl group, an amino group, an aminopropyl group, or an isopropyl group. The halogen is preferably F, Cl, Br, or I, particularly preferably F.

Among them, nucleosides modified with 2'-fluoro, 2'—O-methyl, or 2'—O-methoxyethyl can be particularly suitably used.

Examples of the cross-linked nucleosides include 2',4'-BNA (bridge nucleic acid, also called LNA (locked nucleic acid)) in which an oxygen atom at position 2' and a carbon atom at position 4' are bridged via a methylene bond (Koshkin et al., J. American Chemical Society, 120: 13252-13253, 1998), $BNA^{COC}$, $BNA^{NC}$, ENA (2'—O,4'—C-ethylene-bridged nucleic acid) (WO2000/047599), cEt BNA, and 4'-thionucleoside in which an oxygen atom of a furanose ring is replaced with a sulfur atom (Dande, P., et al., J. Med. Chem., 49:1624-1634, 2006, and WO2004/18494).

Among them, LNA or ENA is particularly preferred, and ENA is most preferred.

Examples of the substituted nucleosides include nucleosides substituted with a morpholino ring (also referred to as morpholino) (see U.S. Pat. No. 5,034,506).

Examples of the nucleosides with a modified base moiety include uridine and cytidine modified at position 5 (e.g., 5-(2-amino)propyluridine and 5-bromouridine), adenosine and guanosine modified at position 8 (e.g., 8-bromo-guanosine), deazanucleotides (e.g., 7-deazaadenosine), and O- and N-alkylated nucleosides (e.g., N6-methyladenosine).

The ASO according to the present invention preferably consists of 18 to 30 nucleotides. Preferably, 20% or more nucleosides in all nucleosides undergo the modification, more preferably sugar moiety modification. Particularly, in the case of using ENA, 20 to 50% nucleosides are preferably ENA. This is because if more than 50% nucleosides are ENA, the effect of the present invention may not be obtained due to a strengthened buffering effect in terms of high-order functions. In the case of using morpholino, 100% nucleosides are preferably morpholino.

The ASO according to the present invention may further have a bond such as a phosphorothioate bond (sulfurization), a phosphorodithioate bond, or a phosphoramidate bond between nucleosides, in addition to the sugar moiety modification or the base moiety modification. Among them, a phosphorothioate bond is preferred.

Any of the modifications are techniques known in the art, and are routinely used as methods for improving the in vivo stability of oligonucleic acids (see Summerton and Weller, Antisense Nuc. Acid Drug Dev., 7: 187-195 (1997); and Hyrup et al., Bioorgan. Med. Chem., 4: 5-23 (1996)).

A peptide, an aptamer, a hydrophobic molecule, or the like may be conjugated to the terminal (5'-terminal and/or 3'-terminal) nucleotide of the microRNA according to the present invention or the precursor, for the purpose of tissue-specific delivery or improvement in cell membrane permeability. Examples of the hydrophobic molecule suitable for this purpose include cholesterol, vitamin E ($\alpha$-tocopherol), and a palmitoyl group (WO2005/115481, and Uno Y., et al., Human Gene Therapy, 22:711-719,2011).

The modifications may be used in combination.

The oligonucleotide according to the present invention has a nucleotide sequence comprising one or more nucleotide sequences represented by SEQ ID NO: 2 that are consecutively connected. The number of repetitions of the sequence of SEQ ID NO: 2 may be 1. When the number is 1, it is preferable that the oligonucleotide includes a nucleotide sequence complementary to a start site of the GGCCTG repeat region of NOP56 pre-mRNA. This is because the oligonucleotide exerts an excellent effect of inhibiting the formation of RNA foci, even though only one molecule of the oligonucleotide can bind to one molecule of NOP56 pre-mRNA having SCA36 mutation. The oligonucleotide can be expected to produce high therapeutic effects at low doses and is therefore very useful.

Examples of such a nucleotide sequence can include the nucleotide sequence represented by SEQ ID NO: 10. In the present invention, an oligonucleotide having the nucleotide sequence represented by SEQ ID NO: 10 and being modified at the sugar moiety and/or the base moiety as described above can be suitably used. Examples of the suitable oligonucleotide include the oligonucleotide represented by SEQ ID NO: 10.

Examples of the oligonucleotide having a nucleotide sequence comprising two or more nucleotide sequences represented by SEQ ID NO: 2 can include an oligonucleotide having the nucleotide sequence represented by SEQ ID NO: 4. In the present invention, an oligonucleotide having the nucleotide sequence represented by SEQ ID NO: 4 and being modified at the sugar moiety and/or the base moiety as described above can be suitably used. Examples of the suitable oligonucleotide include the oligonucleotide represented by SEQ ID NO: 4.

Composition for Prevention or Treatment of SCA36

The composition for prevention or treatment of SCA36 according to the present invention comprises the ASO effectively suppressing SCA36 RNA foci as an active ingredient. The composition according to the present invention can contain a pharmaceutically acceptable carrier, diluent, excipient, adjuvant, and the like in addition to the active ingredient and can be produced by a pharmaceutical method usually used.

One example of the suitable form of the composition according to the present invention includes a liquid composition. The liquid composition may be produced by dissolving or suspending the active ingredient in a pharmaceutically acceptable liquid carrier. For example, a liquid carrier known in the art, such as water, physiological saline, an injectable aqueous solution, or a Ringer's solution can be used as the liquid carrier, and a pharmaceutically acceptable salt may be further contained therein. When the composition according to the present invention comprises the isolated nucleic acid, a carrier for nucleic acid drugs may be added as the liquid carrier. Examples of such a carrier include cationic lipid and atelocollagen (Japanese Patent No. 5145557). When the composition according to the present invention comprises a nucleic acid encoded in the virus vector, one or more dihydric alcohols or polyhydric alcohols and a nonionic surfactant (e.g., sorbitan esters and TWEEN compounds) may be added as the excipient (see WO00/32233).

The liquid composition according to the present invention may be produced by encapsulating the active ingredient into nanoparticles for drug delivery, and then suspending the nanoparticles in a pharmaceutically acceptable liquid carrier. The nanoparticles for drug delivery are a particle dispersion or solid particles with a particle size of 10 to 1000 nm prepared from diverse materials such as lipids, proteins, polysaccharides, and synthetic polymers. Examples thereof include liposomes, micelle, metal nanoparticles, and polymer nanoparticles. Specific examples of the liposomes include, but are not limited to, liposomes composed mainly of N-[2,3-(dioleoyloxy)propyl]-N,N,N-trimethylammonium chloride (DOTMA) or dioleoylphosphatidylethanolamine (DOPE). The surface of the nanoparticles may be modified with various substances for the purpose of improvement in biocompatibility or delivery characteristics.

These nanoparticles for drug delivery may be produced according to methods well known to those skilled in the art.

In a suitable embodiment, the liquid composition according to the present invention is a dispersion of nanoparticles consisting of poly-lactide-co-glycolide (PLGA) (PLGA nanoparticles) and containing the active ingredient. The average particle size of the PLGA nanoparticles is 50 to 200 nm, more preferably 60 to 150 nm, most preferably 70 to 100 nm, in terms of a value measured by a dynamic light scattering method, and the particle surface may be modified with chitosan. The dispersion may contain a dispersion stabilizer (e.g., polyvinyl alcohol) or a pH adjuster (e.g., citric acid hydrate).

The production of the PLGA nanoparticles and the encapsulation of the active ingredient according to the present invention into the particles may be performed according to, for example, methods described in Japanese Patent No. 4340744. The PLGA nanoparticles are excellent in biocompatibility, biodegradability, and sustained release. Therefore, the aforementioned dispersion of the PLGA nanoparticles containing the active ingredient according to the present invention may be used as an inhalation drug, an intramuscular injection drug, a stent, or the like (see Tsukada Y., et al, New Developments in Polylactic Acid Research, published by Nova Science Publishers, Chapter 6, pp. 153-182, 2015; and Yusuke Tsukada, et al., Development and practical use of new DDS products offered by PLGA nanoparticles. Medicine and Drug Journal, Vol. 50, p. 73-80, 2014).

Administration Method

The composition for prevention or treatment of SCA36 according to the present invention can be administered to a patient by use of a method known in the art. For example, the liquid composition may be systemically administered by intravenous injection or transfusion, or may be locally administered into the ventricle or the medullary cavity using stereotactic injection, a needle or a catheter, an osmotic pump or an infusion pump, a drug eluting stent, or the like. When the composition according to the present invention comprises the active ingredient in a state encoded in a virus vector, the composition may be administered by stereotactic injection to the muscle (preferably skeletal muscle).

Methods for delivering drugs through a needle or a catheter injected into the ventricle or the spinal cord are known in the art (Stein et al., J. Virol, 73: 3424-3429, 1999; Davidson et al., PNAS, 97: 3428-3432, 2000; Alisky and Davidson, Hum. Gene Ther., 11: 2315-2329, 2000; etc.). Drug delivery to the brain using an osmotic pump or an infusion pump is well known as convection-enhanced delivery (CED) (U.S. Pat. No. 6,309,634). For example, U.S. Pat. Nos. 5,735,814, 6,042,579, and 5,814,014 disclose an injection system to the brain using an implantable pump and catheter, and these methods may be used. A large number of apparatuses for delivering drugs to the brain and the spinal cord are also commercially available (e.g., SynchroMed(R), manufactured by EL Infusion System), and these apparatuses may be used.

The dose and the administration frequency can be adjusted according to various factors such as the severity of symptoms, age, and body weight of a subject.

In the present invention, the "healthy subject" means a subject that is not affected by SCA36.

Target Disease

The composition according to the present invention can be suitably administered as a prophylactic or therapeutic drug to a human having the abnormal expansion of GGCCTG repeats (specifically, to 600 or more repeats) intron 1 of NOP56 gene.

Neuron and Motor Neuron

In the present invention, the neurons are defined as cells that express one or more neuron marker genes such as β-III tubulin gene and has neurites (β-III tubulin-positive neurites). In the present invention, the motor neurons are defined as neurons that express one or more motor neuron marker genes such as islet1 and SMI32 genes. In the present invention, neurons and motor neurons having a thickened cell body are also referred to as mature neurons and mature motor neurons, respectively.

EXAMPLES

Hereinafter, the present invention will be described more specifically with reference to Examples. However, the present invention is not limited by these examples by any means. First, main approaches used in Examples of the present application will be described.

Approach 1 Detection of RNA Foci-Positive Cells

RNA foci-positive cells were detected by FISH (fluorescence in situ hybridization) using, as a probe, a 5'-terminally Cy3-fluorescently labeled oligonucleotide (manufactured by GeneDesign, Inc.) having the nucleotide sequence represented by SEQ ID NO: 14 (CCAGGCCCAGGCCCAG) and consisting of 2',4'-BNA (2',4'-bridged nucleic acid, LNA). The oligonucleotide was complementary to a region containing GGCCUG repeats in intron 1 of pre-mRNA of the NOP56 gene, and was used in the detection of RNA foci in autopsied tissues from SCA36 patients. A probe consisting of an oligonucleotide having a sequence complementary to the probe was used as a negative control (hereinafter, referred to as a negative control probe).

Specifically, cells were fixed in 4% paraformaldehyde (10 minutes), permeabilized with 70% ethanol (on ice), and equilibrated with 2×SSC containing 50% formamide (66° C., 30 minutes and the probe (40 nM) denatured in advance was added thereto for hybridization (52° C., 3 hours). Subsequently, the cells were washed with 2×SSC containing 50% formamide (52° C., 20 minutes, twice), further washed with 1×SSC (at room temperature, three times), and then stained with DAPI. Then, ProLong Gold antifade reagent was mounted on the cells, which were then analyzed using LSM710 microscope (manufactured by Carl Zeiss AG) and IN CELL Analyzer 6000.

For RNase treatment, DNase-free RNase A (manufactured by F. Hoffmann-La Roche, Ltd.) was added at 50 μg/ml to the cells thus fixed, and incubated at 37° C. for 1.5 hours.

RNA foci in neurons or motor neurons were detected by treating the cells thus washed with 1×SSC, with a blocking buffer (buffer containing 5% bovine serum albumin and 0.2% Triton X-100) (room temperature, 20 minutes), followed by immunostaining. The primary antibody used was an anti-β-III tubulin antibody (1:2,000; manufactured by Cell Signaling Technology, Inc.) or an anti-Islet1 antibody (1:200; manufactured by Developmental Studies Hybridoma Bank) (4° C., overnight), and the secondary antibody used was conjugated with Alexa (room temperature, 1 hour). The immunostaining was performed using Fluor-conjugated. The cells were washed three times with PBS and then stained with DAPI. ProLong Gold antifade reagent was mounted on the cells, which were then analyzed using LSM710 microscope (manufactured by Carl Zeiss AG) and IN CELL Analyzer 6000.

For analysis, Cy3 signals having a diameter of 0.60 μm or larger were captured as RNA foci, and the number of RNA foci-positive cells was autonomously counted using IN CELL Developer toolbox software 1.92. In the present application, cells having one or more of the RNA foci are regarded as RNA foci-positive cells. All the RNA foci detected in this method were observed within DAPI signals, and therefore, the RNA foci were considered to be formed in the nuclei.

Approach 2 Introduction of ASO to iPSN

Each ASO was added at a final concentration of 400 nM to a culture system of iPSNs derived from healthy subjects or SCA36 patients, and introduced thereto by electroporation using Amaxa™ 4D-Nucleofector™ (manufactured by Lonza Group AG). The cells were cultured for 48 hours after the introduction and variously analyzed. The sequences of the ASOs used in Examples are shown in Table 1.

TABLE 1

| ASO name | Nucleotide sequence and modification pattern | | Infraction of degradation by RNaseH | SEQ ID NO |
|---|---|---|---|---|
| ASO-A | $c^E c^E c^E a^{Met} g^{Met} g^{Met} c^E c^E c^E a^{Met} g^{Met} g^{Met} c^E c^E c^E a^{Met} g^{Met} g^{Met} c^E c^E$ | Phosphorothioate bonds between all nucleotides | Absent | SEQ ID NO: 4 |
| ASO-B | $C^E C^E C^E A^E G^E GCCCAGGCCCA^E G^E G^E C^E C^E$ | | Present | SEQ ID NO: 5 |
| ASO-C | $C^E G^E C^E A^E G^E GCGCAGGCCCA^E G^E G^E C^E C^E$ | | Present | SEQ ID NO: 6 |
| ASO-D | $G^E T^E G^E C^E A^E ACAGCACCTGG^E A^E A^E G^E G^E$ | | Present | SEQ ID NO: 7 |
| ASO-E | $C^E G^E C^E G^E T^E GCTCAAACAGC^E A^E C^E G^E T^E$ | | Present | SEQ ID NO: 8 |
| Control ASO1 | $C^E G^E C^E A^E T^E GCGAAGCCTCTG^E G^E G^E C^E$ | | | SEQ ID NO: 9 |
| ASO-F | $C^M A^M G^M G^M C^M C^M C^M T^M G^M T^M C^M T^M G^M C^M G^M G^M C^M C^M C^M G^M A^M A^M$ | | Absent | SEQ ID NO: 10 |
| ASO-G | $C^M A^M A^M C^M A^M G^M C^M A^M C^M C^M T^M G^M G^M A^M A^M C^M G^M G^M G^M A^M G^M C^M C^M G^M G^M$ | | Absent | SEQ ID NO: 11 |
| ASO-H | $C^M A^M G^M A^M C^M T^M G^M A^M T^M C^M T^M C^M C^M T^M C^M C^M A^M C^M T^M T^M C^M C^M T^M T^M C^M$ | | Absent | SEQ ID NO: 12 |
| Control ASO2 | $C^M C^M T^M C^M T^M T^M A^M C^M C^M T^M C^M A^M G^M T^M T^M A^M C^M A^M A^M T^M T^M T^M A^M T^M A^M$ | | | SEQ ID NO: 13 |

Lower-case characters represent ribonucleotide (RNA).
Superscript "E" represents ENA, "M" represents morpholino, and "Met" represents 2-O-methyl modification.

Significance tests on results obtained in Examples of the present application were conducted by use of the two-tailed Student's t-test or the Dunnett post hoc test. In the case of P value<0.05, it was determined that there was significance.

Example 1 Preparation of Human Neuron Having SCA36 Mutation iPSCs derived from human healthy subjects used were obtained from Riken BioResource Research Center (http://ja.brc.riken.jp/) (Control-1 and -2), or produced according to the method of Mishima et al. (Mishima T, Ishikawa, T, Imamura, K, Kondo, T, Koshiba, Y, Takahashi, R, et al., (2016). Cytoplasmic aggregates of dynactin in iPSC-derived tyrosine hydroxylase-positive neurons from a patient with Perry syndrome. Parkinsonism Relat Disord 30: 67-72.AC) (Control-3).

iPSCs derived from SAC36 patients (SAC36-1 to SAC36-3) were produced according to the method of Okita et al. (Okita, K, Yamakawa, T, Matsumura, Y, Sato, Y, Amano, N, Watanabe, A, et al., (2013). An Efficient Nonviral Method to Generate Integration-Free Human-Induced Pluripotent Stem Cells from Cord Blood and Peripheral Blood Cells. Stem Cells 31: 458-466).

Each iPSC was immunostained to confirm that the expression of undifferentiated cell marker genes (NANOG and SSEA4 genes) was maintained (i.e., the ability to undifferentiate was maintained) (FIG. 1a). It was also confirmed by repeated-primed PCR (see Kobayashi, H, Abe, K, Matsuura, T, Ikeda, Y, Hitorni, T, Akechi, Y, et al., (2011). Expansion of Intronic GGCCTG Hexanucleotide Repeat in NOP56 Causes SCA36, a Type of Spinocerebellar Ataxia Accompanied by Motor Neuron Involvement. Am J Hum Genet 89: 121-130) that the GGCCTG repeat length in intron 1 of the NOP56 gene fell within the normal range for iPSCs derived from Control-1 to Control-3, but was abnormally expanded in SCA36-1 to SCA36-3 (FIG. 1b and Table 2).

TABLE 2

| iPSC clone | Origin | GGCCTG repeat length in intron 1 of NOP56 gene | Remarks |
| --- | --- | --- | --- |
| Control-1 | Peripherial blood mononuclear cell of healthy subject | Normal | Obtained from Riken |
| Control-2 | Peripherial blood mononuclear cell of healthy subject | | BioResource Research Center |
| Control-3 | Peripherial blood mononuclear cell of healthy subject | | Produced by present inventors |
| SCA36-1 | Skin fibroblast of SCA36 patient | Abnormal expansion | |
| SCA36-2 | Peripherial blood mononuclear cell of SCA36 patient | | |
| SCA36-3 | Peripherial blood mononuclear cell of SCA36 patient | | |

These iPSCs were induced to differentiate into neurons by use of SFEBq (quick embryoid body-like aggregate method) (Egawa, N, Kitaoka, S, Tsukita, K, Naitoh, M, Takahashi, K, Yamamoto, T, et al., (2012). Drug Screening for ALS Using Patient-Specific induced Pluripotent Stem Cells. Sci Transl Med 4: 145ra104; and Maury, Y, Come, J, Piskorowski, R A, Salah-Mohellibi, N, Chevaleyre, V, Peschanski, M, et al., (2015). Combinatorial analysis of developmental cues efficiently converts human pluripotent stem cells into multiple neuronal subtypes. Nat Biotechnol 33: 89-96).

Specifically, iPSCs were dissociated into single cells and rapidly reaggregated in a low-adhesion U-shaped 96-well plate. Then, the cell aggregates were cultured in Dulbecco's modified Eagle's medium/Ham's F12 (manufactured by Thermo Fisher Scientific Inc.) medium containing 5% KSR (manufactured by Invitrogen Corp.), minimum essential medium-nonessential amino acids (manufactured by Invitrogen Corp.), L-glutamine (manufactured by Sigma-Aldrich Co. LLC), 2-mercaptoethanol (manufactured by Wako Pure Chemical Industries, Ltd.), 2 µM dorsomorphin (manufactured by Sigma-Aldrich Co. LLC), 10 µM SB431542 (manufactured by Cayman Chemical), 3 µM CHIR99021 (manufactured by Cayman Chemical), and 12.5 ng/mL fibroblast growth factor (manufactured by Wako Pure Chemical Industries, Ltd.) for 11 days. The starting day of the culture in the medium is defined as a differentiation induction start day (i.e., Day 0). On Day 4, 100 nM retinoic acid (manufactured by Sigma-Aldrich Co. LLC) and 500 nM Smoothened ligand (manufactured by Enzo Life Sciences, Inc.) were added thereto, and the cell aggregates were further cultured in neurobasal medium (manufactured by Thermo Fisher Scientific Inc.) containing B27 Supplement (manufactured by Thermo Fisher Scientific Inc.), 100 nM retinoic acid, 500 nM Smoothened ligand, and 10 µM DAPI (manufactured by Selleck Chemicals). On Day 16, the aggregates were dissociated into single cells using Accumax (manufactured by Innovative Cell Technologies, Inc.) and then inoculated to a dish coated with Matrigel (manufactured by BD Biosciences) so that the cells adhered to the dish. Then, the cells were cultured in neurohasal medium containing 10 ng/ml brain-derived neurotrophic factor (manufactured by R&D Systems, Inc.), 10 ng/ml glial cell line-derived neurotrophic factor (manufactured by R&D Systems, Inc.), and 10 ng/ml neurotrophin-3 (manufactured by R&D Systems, Inc.) for 8 days.

Results of immunostaining the cells of Day 24 with antibodies against a neuron marker protein (β-III tubulin) and motor neuron marker proteins (Islet1 and SMI32) are shown in FIG. 1c. In all the cases of inducing the differentiation of iPSCs, a large number of mature neurons having a thickened cell body and elongated β-III tubulin-positive neurites were confirmed (FIG. 1c, upper panels). Furthermore, a large number of β-III tubulin/Islet1 double positive cells (FIG. 1c, upper panels) and SMI32-positive cells (FIG. 1c, lower panels) were also confirmed, and some of these cells were confirmed to differentiate into motor neurons.

Results of analyzing the number of cells positive to each antibody in the immunostaining are shown in FIG. 1d. It is evident that when the differentiation of Control-iPSCs or SCA36-iPSCs was induced, cells of more than half the total number of cells (the number of DAPI-positive cells) were positive to β-III tubulin, i.e., were induced to differentiate into neurons (FIG. 1d, left panel). This is very high differentiation induction efficiency as an approach of inducing differentiation by the addition of neuronal differentiation inducers to a medium. These results further demonstrated that the induction of differentiation of any of the iPSCs involved 20% or more motor neurons (i.e., Islet1-positive cells or SMI32-positive cells) (FIG. 1d, central and right panels). This efficiency is also very high differentiation induction efficiency. These numbers of positive cells had no significant difference between the differentiated cells induced from Control-iPSCs and the differentiated cells induced from SCA36-iPSCs, confirming that SCA36-iPSCs had the ability to differentiate into neurons (including motor neurons) at the same level as in Control-iPSCs.

In the present specification, hereinafter, cells induced from Control-iPSCs and SCA36-iPSCs to differentiate into neurons according to the method are also referred to as Control-iPSNs and SCA36-iPSNs, respectively.

Example 2 Formation of RNA foci in SCA36-iPSN

SCA36-iPSNs were analyzed for whether or not RNA foci would be formed occur therein, as well as in neurons from patients, according to approach 1. The results are shown in FIG. 2.

As shown in the upper panels of FIG. 2a, no probe-derived signal was substantially detected for any of the iPSNs derived from three healthy subjects as Control-iPSNs. Specifically, the neurons derived from healthy subjects were confirmed to not form RNA foci with the GGCCUG repeat region of pre-mRNA of the NOP56 gene as a core.

By contrast, cells having, in the nucleus, strong fluorescent signals of 0.60 µm or larger in diameter derived from the probe (i.e., RNA foci) were confirmed in all the iPSNs derived from three patients as SCA36-iPSNs (FIG. 2a, lower panels). Results of counting the number of positive cells are shown in FIG. 2b. It is evident that RNA foci spontaneously formed in 60% or more cells of SCA36-iPSNs. As a result of further performing immunostaining with an anti-β-III tubulin antibody or an anti-Islet1) antibody (approach 1) following the probe treatment, strong signals derived from the probe were detected in the nuclei of almost all the β-III tubulin-positive cells or Islet1)-positive cells.

These results demonstrated that RNA foci with the GGCCUG repeat region in NOP56 pre-mRNA as a core spontaneously formed in neurons and motor neurons obtained by inducing the differentiation of iPSCs derived from SCA36 patients.

Although results are omitted, no probe-derived signal was substantially detected in both Control-iPSNs and SCA36-iPSNs by using a probe having a nucleotide sequence complementary to the probe (negative control probe instead of the probe. No probe-derived fluorescent signal was detected when SCA36-iPSNs were treated with RNaseA after the probe treatment.

Accordingly, the fluorescent probe-derived signals detected in SCA36-iPSNs were confirmed to result from the hybridization of the probe to the GGCCUG repeat region in NOP56 pre-mRNA, not the hybridization to the NOP56 gene i.e., DNA).

Example 3 Inhibition of Formation of RNA foci by ASO

Next, ASO capable of effectively suppressing a spontaneous formation of RNA foci in SCA36-iPSNs was studied.

Five types of ASOs (ASO-A to -E) described in Table 2 were introduced to Control-iPSNs and SCA36-iPSNs according to [Approach 2] and analyzed for the presence or absence of RNA foci according to [Approach 1]. The target site of each ASO is shown in FIG. 3a. As is evident from FIG. 3a and Table 1, ASO-A and ASO-B each consist of a sequence having consecutive repeats of a nucleotide sequence (SEQ ID NO: 2) complementary to the GGCCUG sequence. Therefore, a plurality of molecules are capable of binding into the repeat region. By contrast, ASO-C to ASO-E are capable of binding by only one molecule to a particular site in NOP56 pre-mRNA. Only ASO-A is block type, and ASO-B to ASO-E are gapmer type.

In the case of introducing Control-ASO1, a large number of cells having RNA foci were found (FIG. 3b, uppermost panels). In the case of introducing ASO-A to -E, cells having RNA foci were found only slightly in SCA36-iPSNs derived from any of the patients (FIG. 3b, second or later panels from the top). FIG. 3c shows results of measuring the number of cells having RNA foci. In the case of introducing gapmer ASO-B to -E, the number of cells having RNA foci was drastically decreased as compared with the control (iPSNs harboring the negative control probe). In the case of introducing block ASO-A, the number of RNA foci-positive cells was also decreased to the same level as in the gapmer ASO (FIG. 3c).

By contrast, the expression level of NOP56 mRNA (mature mRNA level) tended to be more markedly reduced than the control by introducing ASO-B to -E, whereas no reduction in expression level was found in the introduction of ASO-A (FIG. 3e). The expression level of NOP56 mRNA in iPSNs derived from SCA36 patients was already significantly decreased more than that in iPSNs derived from healthy persons without the introduction of ASO (FIG. 3d).

Accordingly, even block ASO was shown to be able to inhibit the formation of RNA foci, without inducing the cleavage of NOP56 pre-mRNA, at the same level as in gapmer ASO capable of inducing the cleavage of target RNA as long as a plurality of ASO molecules can bind into the repeat region.

Block ASO capable of binding by only one molecule to NOP56 pre-mRNA was further prepared and studied for its effect.

As is evident from Table 1 and FIG. 4a, ASO-F to -H are modified with morpholino and are therefore ASOs capable of binding by only one molecule to NOP56 pre-mRNA, without inducing the cleavage of target RNA by RNaseH. Among them, ASO-F is ASO that has only one nucleotide sequence (SEQ ID NO: 2) complementary to the GGCCUG sequence and binds to a start site of the repeat region of NOP56 pre-mRNA. ASO-G and ASO-H have no nucleotide sequence (SEQ ID NO: 2) complementary to the GGCCUG sequence and are therefore ASOs binding to a moiety other than the repeat region of NOP56 pre-mRNA, In the case of introducing ASO-F, the number of cells having RNA foci and the area of the RNA foci were drastically decreased in SCA36-iPSNs derived from any of the patients as compared with the control (FIGS. 4c and 4d). By contrast, ASO-G and ASO-H introduced exhibited no significant difference from the control in some cases and did not exert a stable suppressive effect (FIGS. 4c and 4d).

Accordingly, even block ASO which binds by only one molecule to NOP56 pre-mRNA was shown to be able to effectively inhibit the formation of RNA foci as long as the ASO comprises one or more nucleotide sequences (SEQ ID NO: 2) complementary to the GGCCUG sequence and targets the start site of the repeat region.

These results demonstrated that the antisense oligonucleotide that has a nucleotide sequence comprising one or more consecutive repeats of a nucleotide sequence (SEQ ID NO: 2) complementary to the GGCCUG sequence and can stably bind to human NOP56 pre-mRNA without being targeted by RNaseH can effectively suppress a spontaneous formation of RNA foci in neurons having SCA36 mutation.

What is claimed is:

1. An oligonucleotide comprising the entire nucleobase sequence of SEQ ID NO: 2 or a nucleobase sequence in which two or more of the entire nucleobase sequences of SEQ ID NO: 2 are consecutively connected, wherein
the oligonucleotide is complementary to pre-mRNA of a NOP56 gene;
a structure formed by the hybridization of the oligonucleotide to the pre-mRNA does not induce a cleavage of the pre-mRNA by RNaseH;
20% or more of nucleosides of the oligonucleotide with respect to all nucleosides of the oligonucleotide comprise a modified sugar moiety;
the nucleosides comprising the modified sugar moiety are one or more selected from the group consisting of 2'-modified nucleosides and cross-linked nucleosides, the 2'-modified nucleosides being one or more selected from the group consisting of 2'-fluoronucleoside, 2'—O-methylnucleoside and 2'—O-methoxyethylnucleoside, and the cross-linked nucleosides being one or more selected from the group consisting of BNA, ENA, and LNA;
at least one of the nucleosides comprising the modified sugar moiety is ENA; and
the oligonucleotide has the entire nucleobase sequence of SEQ ID NO: 4, nucleosides at positions 1-3, 7-9, 13-15 and 19-20 of SEQ ID NO: 4 are ENA and nucleosides at positions 4-6, 10-12, 16-18 of SEQ ID NO: 4 are 2'—O-methylribonucleosides.

2. The oligonucleotide according to claim 1, wherein the oligonucleotide does not comprise four or more consecutive deoxynucleosides.

3. The oligonucleotide according to claim 1, wherein the oligonucleotide has at least one or more modified internucleoside bonds.

4. The oligonucleotide according to claim 3, wherein the modified internucleoside bonds are phosphorothioate internucleoside bonds.

5. The oligonucleotide according to claim 1, wherein the oligonucleotide consists of 18 to 30 nucleotides.

6. A composition for reducing a number of RNA foci in a cell of a patient suffering from spinocerebellar ataxia type 36, comprising the oligonucleotide according to claim 1 as an active ingredient.

7. An oligonucleotide comprising the entire nucleobase sequence of SEQ ID NO: 10, wherein
the oligonucleotide is complementary to pre-mRNA of a NOP56 gene; and
a structure formed by the hybridization of the oligonucleotide to the pre-mRNA does not induce a cleavage of the pre-mRNA by RNaseH.

8. A composition for reducing a number of RNA foci in a cell of a patient suffering from spinocerebellar ataxia type 36, comprising the oligonucleotide according to claim 7 as an active ingredient.

* * * * *

SEQUENCE LISTING

<160> NUMBER OF SEQ ID NOS: 14

<210> SEQ ID NO 1
<211> LENGTH: 6
<212> TYPE: DNA
<213> ORGANISM: Homo sapiens

```
<220> FEATURE:
<223> OTHER INFORMATION: repeat unit in the intron 1 of NOP56 gene

<400> SEQUENCE: 1 ggcctg                                                                    6

<210> SEQ ID NO 2
<211> LENGTH: 6
<212> TYPE: DNA
<213> ORGANISM: Homo sapiens
<220> FEATURE:
<223> OTHER INFORMATION: complementary sequence to the repeat unit in
      the intron 1 of NOP56 pre-mRNA

<400> SEQUENCE: 2 caggcc                                                                    6

<210> SEQ ID NO 3
<211> LENGTH: 6
<212> TYPE: RNA
<213> ORGANISM: Homo sapiens
<220> FEATURE:
<223> OTHER INFORMATION: repeat unit in the intron 1 of NOP56 pre-mRNA

<400> SEQUENCE: 3 ggccug                                                                    6

<210> SEQ ID NO 4
<211> LENGTH: 20
<212> TYPE: RNA
<213> ORGANISM: Artificial sequence
<220> FEATURE:
<223> OTHER INFORMATION: ASO-A, ENA at positions 1-3, 7-9, 13-15, &
      19-20, 2'-O-methylribonucleosides at positions 4-6, 10-12, 16-18,
      all nucleotides are phosphorothioated.

<400> SEQUENCE: 4
cccaggccca ggcccaggcc                                                    20

<210> SEQ ID NO 5
<211> LENGTH: 20
<212> TYPE: DNA
<213> ORGANISM: Artificial sequence
<220> FEATURE:
<223> OTHER INFORMATION: ASO-B, ENA at positions 1-5, 16-20,  all
      nucleotides are phosphorothioated.

<400> SEQUENCE: 5
cccaggccca ggcccaggcc                                                    20

<210> SEQ ID NO 6
<211> LENGTH: 20
<212> TYPE: DNA
<213> ORGANISM: Artificial sequence
<220> FEATURE:
<223> OTHER INFORMATION: ASO-C, ENA at positions 1-5, 16-20,  all
      nucleotides are phosphorothioated.

<400> SEQUENCE: 6
cgcaggcgca ggcccaggcc                                                    20

<210> SEQ ID NO 7
<211> LENGTH: 20
<212> TYPE: DNA
<213> ORGANISM: Artificial sequence
```

```
<220> FEATURE:
<223> OTHER INFORMATION: ASO-D, ENA at positions 1-5, 16-20, all
      nucleotides are phosphorothioated.

<400> SEQUENCE: 7
gtgcaacagc acctggaagg                                                    20

<210> SEQ ID NO 8
<211> LENGTH: 20
<212> TYPE: DNA
<213> ORGANISM: Artificial sequence
<220> FEATURE:
<223> OTHER INFORMATION: ASO-E, ENA at positions 1-5, 16-20, all
      nucleotides are phosphorothioated.

<400> SEQUENCE: 8
cgcgtgctca aacagcacgt                                                    20

<210> SEQ ID NO 9
<211> LENGTH: 21
<212> TYPE: DNA
<213> ORGANISM: Artificial sequence
<220> FEATURE:
<223> OTHER INFORMATION: Control-ASO1, ENA at positions 1-5, 17-21, all
      nucleotides are phosphorothioated.

<400> SEQUENCE: 9
cgcatgcgaa gcctctgggc c                                                  21

<210> SEQ ID NO 10
<211> LENGTH: 22
<212> TYPE: DNA
<213> ORGANISM: Artificial sequence
<220> FEATURE:
<223> OTHER INFORMATION: ASO-F, all nucleotides are Morpholino.

<400> SEQUENCE: 10
caggccctgt ctgcggcccg aa                                                 22

<210> SEQ ID NO 11
<211> LENGTH: 25
<212> TYPE: DNA
<213> ORGANISM: Artificial sequence
<220> FEATURE:
<223> OTHER INFORMATION: ASO-G, all nucleotides are Morpholino.

<400> SEQUENCE: 11
caacagcacc tggaacggga gccgg                                              25

<210> SEQ ID NO 12
<211> LENGTH: 25
<212> TYPE: DNA
<213> ORGANISM: Artificial sequence
<220> FEATURE:
<223> OTHER INFORMATION: ASO-H, all nucleotides are Morpholino.

<400> SEQUENCE: 12
cagactgatc tcctccactt ccttc                                              25

<210> SEQ ID NO 13
<211> LENGTH: 25
<212> TYPE: DNA
<213> ORGANISM: Artificial sequence
<220> FEATURE:
<223> OTHER INFORMATION: ASO-H, all nucleotides are Morpholino.
```

```
<400> SEQUENCE: 13
cctcttacct cagttacaat ttata                                      25

<210> SEQ ID NO 14
<211> LENGTH: 16
<212> TYPE: DNA
<213> ORGANISM: Artificial sequence
<220> FEATURE:
<223> OTHER INFORMATION: Probe for RNA foci-detection.

<400> SEQUENCE: 14
ccaggcccag gcccag                                                16
```